United States Patent [19] [11] 4,309,990
Brooks et al. [45] Jan. 12, 1982

[54] FOAM MEDICAL CAST

[76] Inventors: William R. Brooks; Irving C. Heinzel, both of 139 W. Commercial Ave., Addison, Ill. 60101

[21] Appl. No.: 178,567

[22] Filed: Aug. 15, 1980

[51] Int. Cl.$^3$ .............................................. A61F 5/04
[52] U.S. Cl. ...................................................... 128/90
[58] Field of Search ................ 128/89 R, 90, DIG. 19

[56] References Cited

U.S. PATENT DOCUMENTS

| | | | |
|---|---|---|---|
| 3,563,234 | 2/1971 | Umstead | 128/90 |
| 4,060,075 | 11/1977 | Blomer et al. | 128/90 |
| 4,108,169 | 8/1978 | Parker | 128/90 |

FOREIGN PATENT DOCUMENTS

| | | | |
|---|---|---|---|
| 2507829 | 9/1976 | Fed. Rep. of Germany | 128/90 |
| 2041758 | 9/1980 | United Kingdom | 128/90 |

*Primary Examiner*—C. Fred Rosenbaum
*Attorney, Agent, or Firm*—John S. Fosse

[57] ABSTRACT

A foam medical cast is formed by dispensing a bead of a pressurized polyurethane prepolymer composition onto a bandage strip making a cast preform. The dispensed prepolymer composition is allowed to expand and foam under ambient conditions, and the resultant preform is wrapped over an undergarment disposed on a human body part to be immobilized. The undergarment is premoistened and the wrapped cast preforms are moistened in order to activate the prepolymer composition. The cast is then allowed to cure to a rigid foam material.

8 Claims, No Drawings

FOAM MEDICAL CAST

FIELD OF THE INVENTION

This invention relates generally to the medical arts and more particularly to the various kinds of braces, casts and splints that are used in such arts to immobilize, support and protect a fractured or otherwise injured human body part.

BACKGROUND OF THE INVENTION

The healing of broken bones, damaged ligaments, arthritic joints and the like is oftentimes promoted by mechanical immobilization; and heretofore, surgical casts molded from layers of gauze-wrapped plaster of Paris have been rather widely employed for this purpose. The drawbacks of plaster casts, however, are well recognized. Rigid plaster dressings are notoriously heavy, cumbersome and uncomfortable. In addition, they exhibit low cast strength and resist the free circulation of air to an encased body part, air circulation being necessary to preserve the health of bandaged skin tissue.

Attempts have been made in the past to overcome the excessive weight and comparative fragility of plaster casts by fabricating thermoplastic resinous material into strips which may be warmed and shaped to the limb or other body part. These strips, however, must be heated in an oven to above 125° F. in order to make them pliable, and then wrapped quickly on the patient. The temperatures involved closely approximate and sometimes exceed human tolerance levels; and this approach has, as a consequence, achieved no great popularity.

Casts of polyurethane which is foamed and shaped in situ have also been proposed. The prior art formulations used for this purpose, however, have required the chemical reaction of two separate components in place on the patient, thus exposing both the patient and his physician to the toxicity of the isocyanate component and to the heat of the exothermic reaction. Despite the obvious strength and low weight advantages of foamed polyurethane, medical casts of this material have not proved of general acceptability heretofore.

BRIEF DESCRIPTION OF THE INVENTION

The present invention provides a scheme for forming medical casts of polyurethane foam material, using the familiar techniques involved in conventional plaster casting, allowing the cast to be molded to fit the patient exactly, but without exposing the patient to either excessive temperatures or any appreciable toxicity hazard. The resultant surgical cast is extremely lightweight, strong and shock-resistant and is not adversely affected by atmospheric moisture, by accidental immersion in water, or by body fluids such as sweat. These and other advantages are achieved by the use of a partially blocked prepolymer which is held under pressure and dispensed onto fabric strips where it is allowed to expand fully before being wrapped over the human body part to be immobilized. A general object of the invention is therefore to provide a new and improved medical cast and a method of tailoring such a cast to each individual patient.

DETAILED DESCRIPTION OF THE INVENTION

The present invention provides a process for the on-site production of a medical cast from a foamable composition which comprises a mixture of a prepolymer or polymer precursor which is curable on contact with a source of water, and a polymer-soluble inert blowing agent. The composition is held under such a superatmospheric pressure that the blowing agent exists in substantially condensed or liquid form. In addition, the composition is capable of expanding, on release of the pressure, due to vaporization of the blowing agent, forming a foam which then cures, on contact with catalyzing amounts of water, without any substantial change in volume.

The prepolymer used in the process of the invention may be any water-catalyzable liquid prepolymer or polymer precursor that, at ambient temperature, has a sufficiently low viscosity to enable it to be dispensed at the desired rate but a sufficiently high viscosity to enable a stable foam or froth to be produced, the foam or froth remaining substantially unchanged in volume until cure of the polymer has taken place.

Polyurethane prepolymers are particularly suitable for use in the process of the invention since they are water-catalyzable and hence may be cured by the moisture in the atmosphere or by a simple spray of atomized water droplets. Polyurethane prepolymers have been fully described in the prior art and the factors influencing their viscosity are well known. In general, a polyurethane prepolymer is obtained by reacting an organic polyol with a controlled amount of an organic polyisocyanate, the product having unreacted isocyanate radicals which function to cure the resinous mass upon exposure to water.

Polyurethane prepolymers for use in making medical casts in accord with the invention may be prepared from any organic polyisocyanate that is liquid at ambient temperature and any organic polyol which has a molecular weight of at least about 300 and which is also liquid at ambient temperature.

Several polyisocyanates have been described in the prior art for use in polyurethane processes, such as tolylene diisocyanate which is available as the 2,4-isomer or as mixtures of the 2,4- and 2,6-isomers. Any of the available grades may be used in distilled or crude form. Also useful are the crude diphenylmethane diisocyanage compositions, particularly those containing from 30% to 90%, preferably from 40% to 80%, by weight of diphenylmethane diisocyanates, the remainder being polyisocyanates of functionality greater than two.

Organic polyols suitable for use in making the polyurethane prepolymers of the invention include reaction products of one or more alkylene oxide compounds with a hydrogen-donor compound, such as ethylene glycol, propylene glycol, glycerol, sorbitol and the various amino-alcohols. These reaction products desirably have molecular weights of between 300 and 8000 according to the amount of alkylene oxide reacted with the active hydrogen-containing compound. Other suitable polyols are polyesters which may be made, for example, from polycarboxylic acids and polyhydric alcohols.

The prepolymers of the invention are prepared by reacting the organic polyisocyanate with the organic polyol in known manner. The viscosity of the prepolymer will depend upon the constitution of the starting materials and on the amount of unreacted isocyanate. In general, the use of a polyol having a high functionality and a high hydroxyl number gives high viscosity prepolymers while the use of appreciable excesses of polyisocyanate tends to reduce the viscosity.

Prepolymers for use in the invention may conveniently be made by reacting an organic polyol with from 2 to 5 mol equivalents of an organic polyisocyanate. For a rigid foam, the use of approximately 3 to 4 mol equivalents of polyisocyanate per mol of polyol has been found to be preferable.

The blowing agent used in the invention is a material which is medically safe, which is inert towards the other ingredients of the system, and which has a sufficiently low boiling point to enable it to vaporize rapidly when the pressure is released. Suitable inert blowing agents are those that have already been proposed for use in making polyurethane foams, including halogenated hydrocarbons having boiling points not exceeding about 50° C. at atmospheric pressure and particularly fluorinated hydrocarbons. Dichlorodifluoromethane is a particularly suitable blowing agent because of its low boiling point. In situations where it is desired to use lower pressures, a mixture of dichlorodifluoromethane and trichlorofluoromethane is more suitable because of the lower volatility of such a mixture. The amount of blowing agent in the foamable compositions may be varied according to the foam density which it is desired to achieve and may range from 10% to 100% or more based on the weight of prepolymer.

The foamable compositions prepared in accordance with the invention may also contain other conventional ingredients of polyurethane foam formulations, including catalysts and surfactants. Suitable catalysts may be of the organic metal compound type. Such catalysts accelerate prepolymer formation when introduced into the polyol or polyisocyanate before the prepolymer has been formed and they subsequently accelerate moisture curing of the foam. Suitable surfactants, which include organosilicon polymers, serve to stabilize the foam until cure has taken place.

The foamable compositions of the present invention are converted into foamed plastics material by releasing the pressure thereon. On reducing the pressure, the foamable composition expands rapidly to give a froth, the final volume of which is rapidly attained. Because foaming is entirely due to the release of pressure and not to vaporization caused by the heat resulting from a chemical reaction, the volume of the froth remains substantially unchanged after attainment of ambient pressure has taken place. This feature is of particular advantage since it precludes putting the pressure of post-expansion on the patient's limb. There is thus a marked contrast between the process of the invention and those prior art processes of medical cast formation in which foaming is caused by a combination of pressure reduction and chemical reaction and in which the volume of the froth increases from 3 to 6 times after having been dispensed into ambient conditions.

Cure of the polymeric froth takes place initially on the surface and then proceeds inwardly of the foam mass due to the diffusion of moisture into the foam. The foam produced has closed cells and is selected to be rigid in order to provide proper mechanical support for the immobilized human body part. Such rigid foams are produced from polyols having from 3 to 8 hydroxyl groups per molecule and hydroxyl numbers of from 200 to 800, preferably 400 to 600.

The foamable compositions of the invention are prepared in bulk and then charged into containers of appropriate size, the pressure being releasable at the time of cast making by some convenient valve arrangement. The containers may vary in size according to the volume of the cast that is to be made.

In addition to a supply of pressurized containers filled with a water-catalyzable polyurethane prepolymer composition, the making of medical casts according to the present invention requires the availability of elongate bandage strips. While surgical gauze may be used, a stronger form of thin, unsized, loosely woven fabric is of particular advantage, such as the multiple-ply fabric frequently called "cheesecloth". Strips of the selected fabric material approximately four inches wide and about 30 inches long have proved to be convenient to handle.

Provision of a suitable undergarment to wrap on the patient's limb is also highly desirable to serve as a foundation for the polyurethane foam; and a fully reticulated or open-pore, flexible, polyester polyurethane foam pad approximately ¼-inch thick has proved eminently useful for this purpose. A medical grade foam having a soft, downy surface texture with up to 100 pores per lineal inch is preferred. Such foam materials may be sterilized by gas, autoclaving or irradiation and exhibit desirably high air permeability. The individual undergarment is readily cut from flexible foam sheet stock using ordinary scissors and can be temporarily secured in place with a few strips of adhesive tape.

With all of the necessary supplies at hand and assuming for purposes of illustration that a patient's broken forearm is to be immobilized, the fractured bone will first be set in the usual way and the injured limb will then be wrapped with the flexible, reticulated foam undergarment, the foam pad being taped in place. At the same time, a number of strips of cheesecloth bandage approximately four inches wide are cut to length, and an individual elliptical bead of incipiently expanding polyurethane prepolymer composition will be dispensed onto each bandage strip inboard from the edges thereof to make a suitable number of cast preforms. Leaving unfoamed tails of the cheesecloth material approximately three to six inches long facilitates handling and applying the cast preforms to the broken arm. Before actual application to the limb, the dispensed prepolymer composition is allowed to expand and foam under the action of the component blowing agent. This expansion takes place under ordinary ambient conditions and is allowed to achieve complete volumetric expansion in order to avoid the possibility of placing post-expansion pressures on the injured limb. In addition, while the prepolymer composition is foaming, it imbeds itself in the bandage strip thereby minimizing any tendency for the foam material to slide off the cloth bandage during application to the injured limb. The fabric also serves to reinforce the foam mechanically in the finished cast. Ordinarily, the dispensed foam is allowed to stand for about two to three minutes and less than about five minutes in order to accomplish full volumetric expansion. A slight amount of surface cure or glaze may occur about six to seven minutes after dispensing due to cross-linking of the prepolymer that is catalyzed by atmospheric moisture.

Before the cast preforms are applied, the wrapped undergarment is advantageously moistened by overspraying with a mist of water droplets. Thereafter, the cast preforms may be wrapped over the moistened undergarment in a generally spiral overlapping pattern so that the foam embeds the edge of the preceedingly wrapped section of the bandage strip. Application is of course performed while the prepolymer composition is in a plastic condition. At this juncture, the physician is able to spread and shape the foam because it will not set up or cure to a rigid state until moisture has fully infused the prepolymer mass and cross-linking is completed by the resultant catalysis. Handling of the foam in its plastic state is advantageously accomplished using disposable plastic gloves because the foam is somewhat tacky and adherent until it has completely cured.

The physician wraps a suitable number of the cast preforms about the injured limb; and when a spiral pattern of application is employed, shallow channels are built into the incipiently reacting foam, generating shallow air passageways. In compliance with the features of the invention, the expanded and foamed prepolymer composition is manipulated into direct contact with the moistened undergarment, forming a monolithic structure therewith. A mist of water droplets is sprayed or atomized over the exterior of the shaped preform in order to accelerate cross-linking, complete cure of the prepolymer mass thereafter taking place in approximately 15 to 30 minutes.

No shrinkage occurs during curing of the foam, thus eliminating another of the disadvantages of plaster of Paris dressings. Finally, an appearance or cleanliness sleeve may be slipped over the cast as an overwrap.

It is to be appreciated that the present invention provides a strong, lightweight medical cast that affords a degree of air-permeability not available with plaster casts. For example, a full-arm cast according to the invention approximately one-half inch thick weighs a total of about 4½ ounces whereas a comparable plaster dressing weighs many pounds. Moreover, medical casting according to the present invention vastly reduces the amount of the physician's time required for a given procedure. Additionally, medical casting according to the present invention may be performed at accident sites, even outdoors at winter sports scenes, because a prepolymer is employed and thus environmental temperatures in excess of 70° F. are unnecessary to cure the polyurethane foam.

The specific embodiment herein described is to be considered as being primarily illustrative. Various changes beyond those described will, no doubt, occur to those skilled in the art; and such changes are to be understood as forming a part of this invention insofar as they fall within the spirit and scope of the appended claims.

The invention is claimed as follows:

1. The method of making a foam medical cast comprising the steps of: providing a water-catalyzable polyurethane prepolymer composition under superatmospheric pressure, said composition including a blowing agent; providing an elongate bandage strip; dispensing a bead of said prepolymer composition onto said bandage strip inboard from the edges thereof to make a cast preform; allowing the dispensed prepolymer composition to expand and foam on said strip under ambient conditions; wrapping an undergarment on a human body part to be immobilized; moistening said wrapped undergarment with water; wrapping said cast preform over and about said moistened undergarment while said prepolymer composition is in a plastic state; shaping said preform to said human body part; spraying a mist of water droplets on the exterior of the shaped preform; and allowing the preform to cure to a rigid foam material.

2. The method of making a foam medical cast according to claim 1 wherein a plurality of said cast preforms are wrapped over and about said moistened undergarment.

3. The method of making a foam medical cast according to claim 1 wherein said bandage strip is a thin, unsized, loosely woven fabric.

4. The method of making a foam medical cast according to claim 1 wherein said undergarment is reticulated flexible polyurethane foam.

5. The method of making a foam medical cast according to claim 4 wherein the expanded and foamed prepolymer composition is caused to make direct contact with the moistened undergarment.

6. The method of making a foam medical cast according to claim 1 wherein said polyurethane prepolymer is the reaction product of an organic polyol having a molecular weight of from about 300 to about 8,000 and an organic polyisocyanate; and wherein said polyisocyanate is present in a mol ratio of between 2 and 5 mol equivalents per mol equivalent of said polyol.

7. The method of making a foam medical cast according to claim 1 wherein said blowing agent is a fluorinated hydrocarbon having a boiling point not exceeding about 50° C.

8. A foam medical cast comprising: a flexible polyurethane foam undergarment; a rigid polyurethane cast body wrapped upon said undergarment; and fabric stripping wrapped with said cast body, the rigid polyurethane material invading the pores of said undergarment and the interstices of said stripping to form a monolithic structure.

* * * * *